United States Patent [19]

Heinemann et al.

[11] Patent Number: 5,449,606
[45] Date of Patent: Sep. 12, 1995

[54] DNA ENCODING NEURONAL NICOTINIC ACETYLCHOLINE RECEPTOR COMPOSITIONS CONTAINING THE BETA 4 SUBUNIT

[75] Inventors: Stephen F. Heinemann, La Jolla; Robert M. Duvoisin, Del Mar; Evan S. Deneris, La Jolla, all of Calif.; James W. Patrick, Houston, Tex.

[73] Assignee: The Salk Institute for Biological Studies, La Jolla, Calif.

[21] Appl. No.: 59,502

[22] Filed: May 6, 1993

Related U.S. Application Data

[63] Continuation of Ser. No. 492,555, Mar. 12, 1990, abandoned, which is a continuation-in-part of Ser. No. 170,295, Mar. 18, 1988, abandoned, and a continuation-in-part of Ser. No. 321,384, Mar. 14, 1989, abandoned.

[51] Int. Cl.⁶ ............................................. C12N 15/12
[52] U.S. Cl. ..................... 435/6; 435/64.1; 435/252.3; 435/320.1; 536/23.5
[58] Field of Search ................. 435/69.1, 252.3, 220.1; 436/501; 536/27

[56] References Cited

U.S. PATENT DOCUMENTS 4,518,527 5/1985 Numa et al. ..................... 530/327

OTHER PUBLICATIONS

Nature 311:626–631, (18 Oct. 1984) Leonard et al. Molecular Cloning and expression of cDNAs for the human interneural receptor.
Nature, vol. 328, 221–227, 16 Jul. 1987, Schofield et al. Sequence and functional expression of the GABAA receptor shows a ligand–gated receptor superfamily.
Nucleic Acids Research, vol. 13, 4739–4749, 1985, Hauptmann et al., A novel class of human type I interferons.
Nature, vol. 313, 806–810, 28 Feb. 1985, Jacobs et al., isolation and characterization of genomic and cDNA clones of human erythropoietin.
Anand et al., "Neuronal Nicotinic Acetylcholine Receptors Expressed in Xenopus Oocytes Have a Pentameric Quaternary Structure," *The Journal of Biological Chemistry* 266(17):11192–11198 (1991).
Boulter et al., "Isolation of a cDNA Clone Coding for a Possible Neural Nicotinic Acetylcholine Receptor α–Subunit," *Nature* 319:368–374 (1986).
Cooper et al., "Pentameric Structure and Subunit Stoichiometry of a Neuronal Nicotinic Acetylcholine Receptor," *Nature* 350:235–238 (1991).
Deneris et al., "Primary Structure and Expression of β: A Novel subunit of Neuronal Nicotinic Acetylcholine Receptors," *Neuron* 1:45–54 (1988).
Duvoisin et al., "The Functional Diversity of the Neuronal Nicotinic Acetylcholine Receptors is Increased by a Novel Subunit: β4," *Neuron* 3:487–496 (1989).
Figl et al., "Regions of β4 αβ2 Subunit Chimeras that Contribute to the Agonist Selectivity of Neuronal Nicotinic Receptors," *FEBS* 308:245–248 (1992).
Goldman et al., "Members of a Nicotinic Acetylcholine Receptor Gene Family Are Expressed in Different Regions of the Mammalian Central Nervous System," *Cell* 48:965–973 (1987).
Halvorsen and Berg, "Affinity Labeling of Neuronal Acetylcholine Receptor Subunits with an α–Neurotoxin that Blocks Receptor Function," *The Journal of Neuroscience* 7(8):2547–2555 (1987).
Luetje and Patrick, "Both α–and β–Subunits Contrib- (List continued on next page.)

*Primary Examiner*—Garnette D. Draper
*Assistant Examiner*—John D. Ulm
*Attorney, Agent, or Firm*—Pretty, Schroeder, Brueggemann & Clark; Stephen E. Reiter

[57] ABSTRACT

The present invention discloses a new neuronal nicotinic acetylcholine receptor subunit, β4. The new subunit can form functional combinations with other neuronal nicotinic acetylcholine receptor subunits, including, but not limited to, alpha2, alpha3, alpha4 and beta2. A cDNA clone containing the DNA sequences that encode the novel receptor subunit of the invention has been deposited with the American Type Culture Collection for patent purposes.

21 Claims, 11 Drawing Sheets

OTHER PUBLICATIONS ute to the Agonist Sensitivity of Neuronal Nicotinic Acetylcholine Receptors," *The Journal of Neuroscience* 11(3):837–845 (1991).

Mauron, et al, "Structure of Chicken Genes Encoding the Nicotinic Acetylcholine Receptor Subunits and Their Variants," *Society for Neuroscience Abstracts* 55.10, p. 171 (1985).

Nef et al., "Genes Expressed in the Brain Define Three Distinct Neuronal Nicotinic Acetylcholine Receptors," *EMBO J.* 7:595–601 (1988).

Papke and Heinemann, "The Role of the $\beta_4$-Subunit in Determining the Kinetic Properties of Rat Neuronal Nicotinic Acetylcholine $x_3$-Receptors," *Journal of Physiology* 444:95–112 (1990).

Schoepfer et al., "cDNA Clones Coding for the Structural Subunit of a Chicken Brain Nicotinic Acetylcholine Receptor," *Neuron* 1:241–248 (1988).

Schoepfer et al., "Brain $\alpha$-Bungarotoxin Binding Protein cDNAs and MAbs Reveal Subtypes of This Branch of the Ligand-Gated Ion Channel Gene Superfamily," *Neuron* 5:35–38 (1990).

Vernallis et al., "Achr Gene Products in Chick Ciliary Ganglia: Transcripts, Subunits, and Receptor Subtypes," *Society for Neuroscience Abstracts* 14.9 17:23 (1991).

Wada et al., "Functional Expression of a New Pharmacological Subtype of Brain Nicotinic Acetylcholine Receptor," *Science* 240:330–334 (1988).

Wada et al., "Distribution of Alpha2, ALpha3, Alpha4, and Beta2 Neuronal Nicotinic Receptor Subunit mRNAs in the Central Nervous System: A Hybridization Histochemical Study in the Rat," *The Journal of Comparative Neurology* 284:314–335 (1989).

Whiting et al., "Neuronal Nicotinic Acetylcholine Receptor $\beta$-Subunit Is Coded for by the cDNA Clone $\beta 4$," *FEBS* 219(2):459–463 (1987).

Whiting et al., "Structurally Different Neuronal Nicotinic Acetylcholine Receptor Subtypes Purified and Characterized Using Monoclonal Antibodies," *The journal of Neuroscience* 7(12):4005–4016 (1987).

Whiting et al., "Expression of Nicotinic Acetylcholine Receptor Subtypes in Brain and Retina," *Molecular Brain Research* 10:61–70 (1991).

Whiting and Lindstrom, "Affinity Labelling of Neuronal Acetylcholine Receptors Localizes Acetylcholine-Binding Sites to Their $\beta$-Subunits," *FEBS* 213:(1):55–60 (1987).

Whiting and Lindstrom, "Purification and Characterization of a Nicotinic Acetylcholine Receptor from Rat Brain," *Proc. Natl. Acad. Sci. USA* 84:595–599 (1987).

Whiting et al., "Structural and Pharmacological-Characterizations of the major Nicotinic Acetylcholine Receptor Subtype Stably Expressed in Mouse Fibroblasts," *Molecular Pharmacology* 40:463–472 (1991).

Mishina, et al., "Expression of Functional Acetylcholine Receptor From Cloned cDNAs", *Nature* 307, 604–608 (1984).

Goldman, et al., "Members of a Nicotinic Acetylcholine Receptor Gene Family Are Expressed in Diffrent Regions of the Mammalian Central Nervous System", *Cell* 48: 965–973 (1987).

Whiting et al., "Functional Acetylcholine Receptor in PC12 Cells Reacts With A Monoclonal Antibody to Brain Nicotine Receptors", *Nature*, 327, 515–518 (1987).

Whiting, et al., "Functional Acetylcholine Receptor in PC12 Cells Reacts With A Monoclonal Antibody to Brain Nicotine Receptors", *Nature* 327:515–518 (1987).

Deneris, et al., "Primary Structure and Expression of A Novel Subunit of Neuronal Nicotinic Acetylcholine Receptors", *Neuron* 1, 45–54 (1988).

Boulter, J., Connolly, J., Deneris E., Goldman D., Heinemann S., and Patrick, J., "Functional Expression of Two Neuronal Nicotinic Acetylcholine Receptors From cDNA Clones Identifies a Gene Family", *Proc. Natl. Acad. Sci. USA 84, 7763–7767, 1987)*.

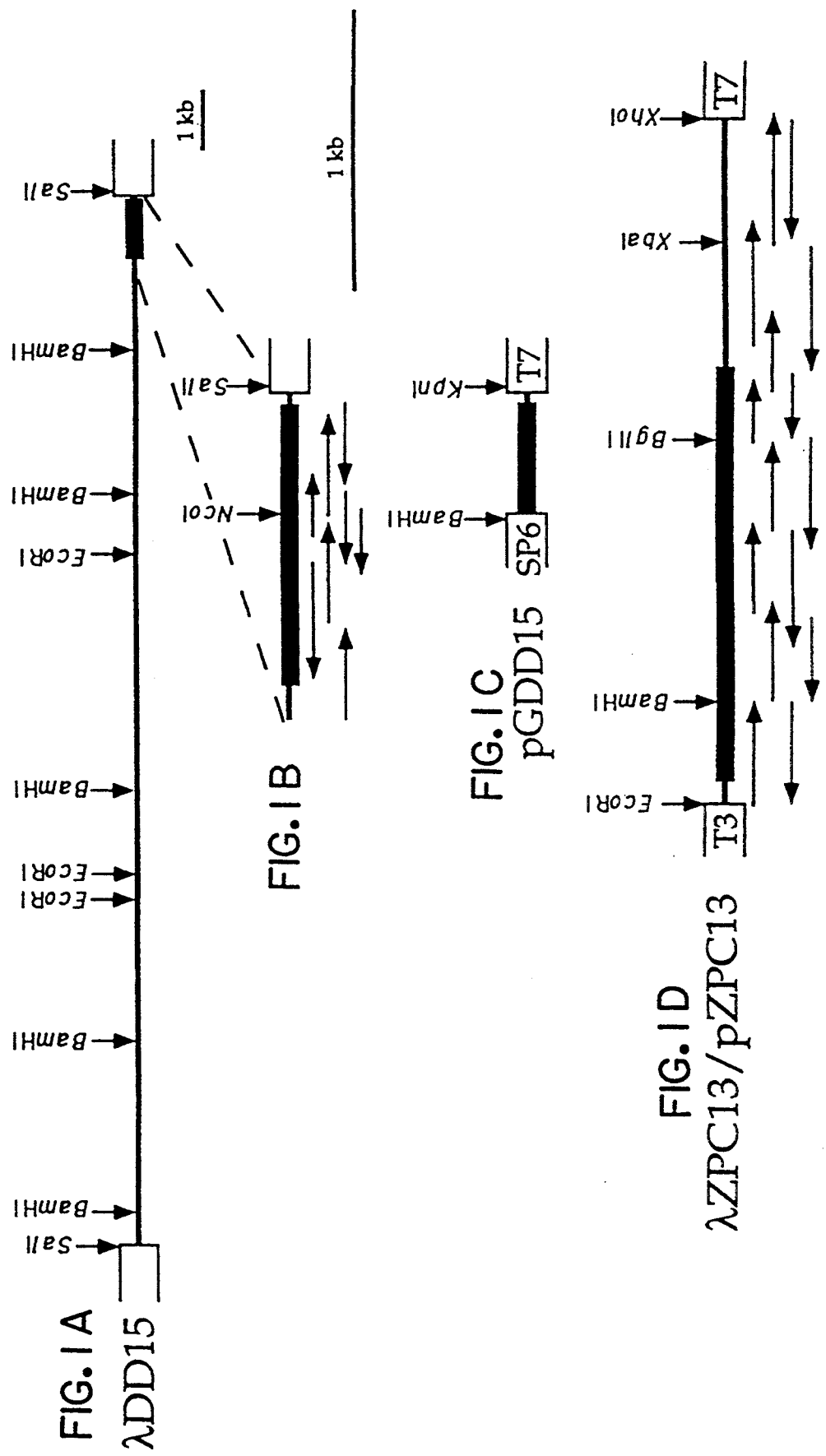

```
  1 CCGGGACATACGCTCACTCGGCGGTTCCATTGTAGAGTGACCGGCTGCCACCGGGCTGGCC

61 ATGAGGGGTACGCCCCCTGCTCCCTGTCTCTCTGTTCTCTCTGCTTCAGGACGGGACTGC
  1 MetArgGlyThrProLeuLeuLeuValSerLeuPheSerLeuLeuGlnAspGlyAspCys

121 CGCCTGGCCAACGCAGAGGAGAAGCTGATGATGACCTCTGAACAAACCCGTACAAC
 21 ArgLeuAlaAsnAlaGluGluLysLeuMetAspAspLeuLeuAsnLysThrArgTyrAsn

181 AACCTGATCCTCGAGAGCATTCGCCGCCACCAGCTCCTCAGTCTCCATCCGCCTGAGCTATCA
 41 AsnLeuIleArgProAlaThrSerSerSerGlnLeuIleSerIleArgLeuGluLeuSer

241 CTGTCCCAGCTCATCAGTGTGAATGAGCGAGAACAGATCATGACCACCAGCATCTGGCTG
 61 LeuSerGlnLeuIleSerValAsnGluArgGluGlnIleMetThrThrSerIleTrpLeu

301 AAACAGGAATGGACTACCGACTACCGCCTGGAACAGCTCCTGCTATGAAGGGTGAAC
 81 LysGlnGluTrpThrThrAspTyrArgLeuAlaTrpAsnSerSerCysTyrGluGlyValAsn

...gtgatgtttctctatgtgcctacccag|
361 ATTCTGAGGATCCCCCGGCAAAGCCGTGTCCTGACATCGTTGTTGTACAACAATGCC
101 IleLeuArgIleProAlaLysArgValTrpLeuProAspIleValLeuTyrAsnAsnAla 421 GATGGCACCTATGAGGTGTCTGTCTACACCAACGTGATTGTGCGTTCCAACGGCAGCATC
121 AspGlyThrTyrGluValSerValTyrThrAsnValIleValArgSerAsnGlySerIle
```

FIG. 3-1

| FIG. 3-1 |
|---|
| FIG. 3-2 |
| FIG. 3-3 |
| FIG. 3-4 |
| FIG. 3-5 |

```
481  CAGTGGCTGCCCCTGCTATCTACAAGAGTGCCTGCAAGATTGAGGTGAAGCACTTTCCC
141  GlnTrpLeuProProAlaIleTyrLysSerAlaCysLysIleGluValLysHisPhePro

541  TTCGACCAGCAGAACTGCACCCTCAAATTCCGCTCCTGGACCTATGACCACACGGAGATT
161  PheAspGlnGlnAsnCysThrLeuLysPheArgSerTrpThrTyrAspHisThrGluIle
                              ◆                                    C
601  GACATGGTTCTTAAGTCGCCCACCGGCCATCATGGATGACTTCACCCCAGTGGTGAATGG
181  AspMetValLeuLysSerProThrAlaIleMetAspAspPheThrProSerGlyGluTrp

661  GACATTGTGGCCCTCCCCAGGAGACGGTGAACCCTCAGGACCCCAGCTACGTGGAT
201  AspIleValAlaLeuProGlyArgArgThrValAsnProGlnAspProSerTyrValAsp

721  GTGACCTATGACTTCATCATCAAGCGCAAGCCGCTCTTCTACACCATCAATCTTATCATT
221  ValThrTyrAspPheIleIleLysArgLysProLeuPheTyrThrIleAsnLeuIleIle
                                                                ┌──
781  CCTTGTGTGCTCATCACCTCGCTGGCTATCCTGCTGCTCTTCTACCTGCCCTCCGACTGTGGG
241  ProCysValLeuIleThrSerLeuAlaIleLeuLeuLeuPheTyrLeuProSerAspCysGly
     ─────────────────────── MSR I ──────────────────────────

841  GAGAAGATGACGCTCTGCATCTCTGTGCTGCTGGCACTCACGTTCTTCCTGCTGCTCATC
261  GluLysMetThrLeuCysIleSerValLeuLeuAlaLeuThrPhePheLeuLeuLeuIle
                                    ──────────── MSR II ─────────
```

FIG. 3-2

```
 901  TCCAAGATCGTGCCTCCCCACCTCCCCTTGACATACCGGCTCATTGGCAAGTACCTCTGTTC
 281  SerLysIleValProProThrSerLeuAspIleProLeuIleGlyLysTyrLeuLeuPhe

961  ACCATGGTGGTGCTGACCTTTCCATCGTCACCACTGTGTCCTCAATGTGCACCAC
 301  ThrMetValLeuValThrPheSerIleValThrThrValCysValLeuAsnValHisHis
                              MSR III

1021  CGCTCACCCAGCACTCACCACCATGGCATCCTGGGTCAAGGAGTGCTTCCTGCACAAACTG
 321  ArgSerProSerThrHisThrMetAlaSerTrpValLysGluCysPheLeuHisLysLeu

1081  CCCACCTTCCTCTTCATGAAGCGTCCCGGTCTTGAAGTCAGTCAGGGTCCTCAGGGTCCTCAT
 341  ProThrPheLeuPheMetLysArgProGlyLeuGluValSerLeuValArgValProHis

1141  CCCAGCAGCAGCTGCACTTGGCACTTGCTCCATGATACTGACCAGCCAGCCACCTCTGCCTTAGGCCCCACC
 361  ProSerGlnLeuHisLeuAlaThrAlaAspThrAlaAlaThrSerAlaLeuGlyProThr

1201  AGCCCATCCAACCTCTATGGGAGTTCCATGTACTTTGTGAACCCTGTCCCTGCCGCTCCT
 381  SerProSerAsnLeuTyrGlySerSerMetTyrPheValAsnProValProAlaAlaPro

1261  AAGTCTGCAGTCAGCTCCCACAGCAGGCCTCCCCAGGATGCCCGTCTGAGTCCTCC
 401  LysSerAlaValSerSerHisThrAlaGlyLeuProArgAspAlaArgLeuArgSerSer

1321  GGGAGGTTCCGGGAAGATCTACAGGAAGCATTAGAGGGTGTCAGTCTTCATCGCCAGCAT
 421  GlyArgPheArgGluAspLeuGlnLeuGluAlaLeuGluGlyValSerPheIleAlaGlnHis
```

FIG. 3-3

```
                |agtcactgccctgcccccacca....
1381  CTGGAGAGGATGACCGAGATCAAAGTGTCATCGAGGACTGGAAGTTCGTGGCGATGGTT
 441  LeuGluSerAspAspArgAspGlnSerValIleGluAspTrpLysPheValAlaMetVal 1441  GTTGACCGGCCTGTTCCTGTGGGTGTTCGTGTTTGTGTATTCTGGGCACCATGGGCTC
 461  ValAspArgLeuPheLeuTrpValPheValCysIleLeuGlyThrMetGlyLeu
                                                    ——— MSR IV ———

1501  TTCCTGCCACCCCTTTCCAGATCCACGCACCCTCCAAGGACTCCTAGGCTACCCGGCGT
 481  PheLeuProProLeuPheGlnIleHisAlaProSerLysAspSer

1561  GCCTCGGG CCGGGTTGTAGTGAGATGATATGAGAAGCCGTGTGGGAAGCTG GGCGTGTC
1621  TTGG CCCGGGTTGTAGTGAGATGATATGAGAAGCCGTGTGGGAAGCTG GGCGTGTCTCGG
1681  GC CCCGGGTTGTAGTGAGATGATATGAGAAGCCGTGTGGGAAGCTG ACTGTTCCATTTGG
1741  GCCATAGCTAATGAGCCCTAAGTAAACAGAGATAAAGCCGTGACTATTGGCAATCAGCCCATCAAACTA
1801  GCCACAGCCACGAGAAGGACACAGAGATAGATGCCTTCTGCTAATCCCTCTGATGCCGTCCA
1861  GTAAGTCCCTGAAGGAGGAGGAGGATGAGGCTGCTGAATACCAGCCTGGCCTCCTTCCTTCCA
1921  CGTGCCAGGCACCGAGTCAGACAGCCGTGTATCATGCCGTCACCCCAGCCCGGCCCTTC
```

FIG. 3-4

1981 CCACCCATCTCCCTCTGATTGGCAGCTACCCCACTAGATTCCCCCACCATCTTTCATTTCC
2041 ATACACTTCTAGATTCTCCCAAGTCAGAACCTTTATATCTTCTACTGCTACCGTCCAAAC
2101 CTCACTGTAAACTCCCAAGCTTTTCACGTGGCTGCACCAGTCAGAGCTCTGCTCCAATGC
2161 CACTTCCTTGTATAAGCCTTCCCATGATCCCTCTGCTCCAGTGTCATTCCTTGTATAAGC
2221 CTTCCCCTAGTCATGCATTGCAAAGCAGTGTCTCCCATAACCACACATCAAATCTCCAGCTTC
2281 CTTGAGTGTTCCCGTCAGTAGCTGCAGCCTTTAGTTGGTGGCACACTAGTCACCAGCAC
2341 CTTGCCCATAAAGTGTATGCTCCATAAGGGCTGGGTGTGTGGATTCACATTCACTCCAG
2401 AGCTTGGGACCCAGCTCTGCACACAGAAGGTGCAAAATAAATGTTTATTGAATGAAAAAA

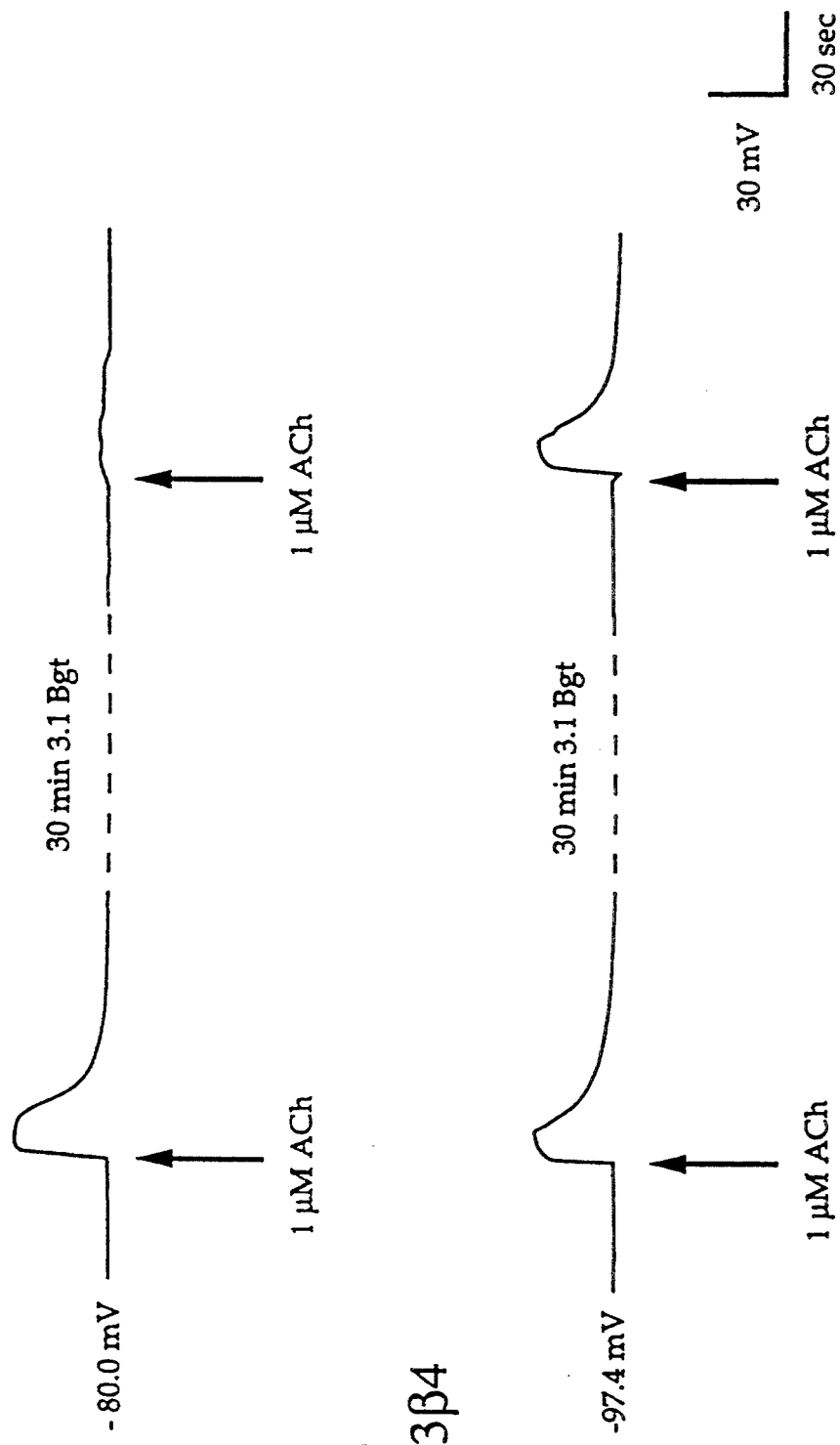

DNA ENCODING NEURONAL NICOTINIC ACETYLCHOLINE RECEPTOR COMPOSITIONS CONTAINING THE BETA 4 SUBUNIT

ACKNOWLEDGMENT

This invention was made with government support under several grants from the National Institutes of Health and the Muscular Dystrophy Association.

RELATED APPLICATION

This application is a continuation of application Ser. No. 07/492,555, filed Mar. 12, 1990, now abandoned, which is a continuation-in-part of application Ser. No. 07/170,295, filed Mar. 18, 1988, now abandoned, and application Ser. No. 07/321,384, filed Mar. 14, 1989, now abandoned.

FIELD OF THE INVENTION

The present invention relates generally to neuronal nicotinic acetylcholine receptor genes and proteins. More particularly, the invention relates to a new subunit member of the family of neuronal nicotinic acetylcholine receptors. The new subunit, named beta4 ($\beta 4$), can participate with known subunits, including alpha-type subunits $\beta 2$, $\beta 3$ and $\beta 4$, and the beta-type subunit, $\beta 2$, (in the presence of at least one alpha subunit), to form previously unknown functional receptors.

BACKGROUND

The diversity of neurotransmitter receptors is far greater than had been anticipated by pharmacological and physiological studies. Two gene superfamilies encode all cloned neurotransmitter receptors: one is the G protein-coupled receptor superfamily, and the other is the ligand-gated ion channel superfamily (for reviews see Hall, 1987; Barnard, et al., 1987). All of the receptors that act through a G protein, for example, the muscarinic acetylcholine receptors, the dopamine receptors, and the $\beta$-adrenergic receptors, are formed by a single polypeptide chain that is postulated to span the plasma membrane seven times. For each class of receptor, a gene family encodes closely related variants that have different pharmacological and physiological characteristics and different patterns of distribution in the nervous system.

In contrast to the G protein superfamily, ligand-gated ion channels are composed of more than one subunit. Expression studies have shown that the diversity of the ligand-gated receptors is due to the presence of the same subunits in different combinations. In addition, multiple genes encode each type of subunit. For example, three types of $GABA_A$ receptor subunits, $\alpha$, $\beta$, and $\gamma$, have been described, and at least for the $\alpha$ and $\beta$ subunits, several genes encode variant subtypes (Schofield, et al., 1987; Levitan, et al., 1988; Pritchett, et al., 1989). In transient transfection assays, functional receptors can be formed by either the $\alpha$ or the $\beta$ subunit alone or in pairwise combinations (Pritchett, et al., 1988). The presence of the $\gamma$ subunit, however, appears to be required for benzodiazepine sensitivity (Pritchett, et al., 1989).

One way to unravel the functional diversity of the nicotinic acetylcholine receptors (NACHRS) in the nervous system is to identify at the molecular level all of the different nAChR subunits. The pharmacology and single-channel characteristics of cloned subunits, expressed in various combinations in transfected cells or in Xenopus oocytes, can then be analyzed. By comparing these results with similar studies performed in vivo, a better understanding of the neuronal nicotinic pathways will become available. In pursuing this effort, the Molecular Neurobiology Laboratory at the Salk Institute for Biological Studies has isolated rat cDNA clones that identify four distinct neuronal nAChR subunits: $\alpha 2$, $\alpha 3$, $\alpha 4$ and $\beta 2$ (see U.S. Ser. Nos. 07/170,295, abandoned, 07/321,384, abandoned and Wada, et al., 1988; Boulter, et al., 1986; Goldman, et al., 1987; Deneris, et al., 1988). Recently, two additional clones that are closely related to the neuronal nAChRs but for which no function has yet been found have been identified. They are referred to as $\alpha 5$ an $\beta 3$ (U.S. Ser. Nos. 07/170,295, abandoned and 07/321,384, abandoned, and Boulter, et al., 1990; Deneris, et al., 1989). The present specification discloses another distinct neuronal nAChR subunit, beta4. In identifying the gene that encodes this subunit, rat genomic libraries were screened with neuronal nAChR cDNA probes. The genes for several of the previously described nAChR subunits were isolated, and their restriction maps were determined. A recombinant phage containing part of the gene for a novel nAChR subunit was also isolated. The primary structure of this subunit was deduced from the nucleotide sequence of a cDNA clone. Expression studies using Xenopus oocytes have shown that this subunit can combine with each of the neuronal $\alpha 2$, $\alpha 3$, and $\alpha 4$ subunits to form functional nAChRs.

The neuronal nAChR subunits are closely related and form a subgroup of the nAChR gene family that also includes the nicotinic receptors present in the Torpedo electric organ and at the vertebrate neuromuscular junction. The latter are formed by the pentameric assembly of four homologous subunits: two $\alpha$ ligand binding subunits and one each of the $\beta$, $\gamma$, and $\delta$ subunits (Reynolds and Karlin, 1978). There is evidence that during development, new nicotinic receptors containing an $\epsilon$ subunit instead of a $\gamma$ subunit are inserted at the neuromuscular endplate (Gu and Hall, 1988). Concomitant with this repopulation, an increase in channel conductance is observed (Sakmann and Brenner, 1978; Mishina, et al., 1986). Functional neuronal nAChRs can be produced by the coinjection into Xenopus oocytes of RNA encoding a $\beta 2$ subunit and one of either an $\alpha 2$, an $\alpha 3$ or an $\alpha 4$ subunit (U.S. Ser. Nos. 07/170,295, abandoned and 07/321,384, abandoned, and Boulter, et al., 1987; Wada, et al., 1988). Whiting and Lindstrom (1986, 1987) have proposed that the nicotinic receptors found in the peripheral and central nervous system are assembled from only two different subunits, an $\alpha$ and a $\beta$ subunit, in a yet undetermined stoichiometry. However, the possibility remains that neuronal nAChRs are composed of more than two distinct subunits.

As those skilled in the art will appreciate, an understanding of the molecular mechanisms involved in neurotransmission in the central nervous system is limited by the complexity of the system. The cells are small, have extensive processes, and often have thousands of synapses deriving from inputs from many different parts of the brain. In addition, the actual number of neurotransmitter receptors is low, making their purification difficult, even under the best of circumstances. Consequently, neither cellular nor biochemical approaches to studying neurotransmission in the central nervous system has been particularly fruitful. This is unfortunate because it is quite probable that the treatment of dementia, Alzheimer's disease and other forms of mental illness will involve modification of synaptic transmission with specific drugs.

The realization that the nicotinic acetylcholine receptors are much more diverse than previously expected offers an opportunity for a level of pharmaceutical intervention and a chance to design new drugs that affect specific receptor subunits. Such subtypes make it possible to observe the effect of a drug substance on a particular subtype. Information derived from these observations will allow the development of new drugs that are more specific, and therefore have fewer unwanted side effects.

In addition, the availability of these neuronal receptors makes it possible to perform initial in vitro screening of the drug substance. While it is true that the drug eventually has to work in the whole animal, it is probable that useful drugs are being missed because conventional screening is limited to average composite effects. Consequently, the ability to screen drug substances in vitro on a specific receptor subtype(s) is likely to be more informative than merely screening the drug substance in whole animals.

Both the receptor subunit DNA and the encoded protein(s) of the present invention can be used for drug design and screening. For example, the cDNA clone encoding the beta4 subunit, alone, or in combination with various alpha subunit clones or other subunit clones, now known or later to be discovered, can be transcribed in vitro to produce mRNA. This mRNA, either from a single subunit clone or from a combination of clones, can then be injected into oocytes where the mRNA will direct the synthesis of the receptor protein. Alternatively, the clones may be placed downstream from appropriate gene regulatory elements and inserted into the genome of eukaryotic cells. This will result in transfected cell lines expressing a specific receptor subtype, or specific combinations of subtypes. The derived cell lines can then be produced in quantity for reproducible quantitative analysis of the effects of drugs on receptor function.

BRIEF DESCRIPTION OF THE DRAWINGS

The drawing comprise six figures, of which:

FIG. 1 is a schematic drawing showing the restriction maps and sequencing strategies. FIG. 1A is the partial restriction map of the genomic insert of λDD15. The solid bar indicates the fifth exon coding region. FIG. 1B is an enlargement of this exon with arrows referring to the extent and direction of nucleotide sequencing reactions. FIG. 1C shows pGDD15, a plasmid used for preparing β4-specific probes; pGDD15 contains an NcoI-SalI fragment of λDD15 encoding a nonconserved segment of the cytoplasmic domain. FIG. 1D shows a partial restriction map and sequencing strategy of the cDNA insert of λZPC13 and its in vivo excised plasmid version pZPC13. See Experimental Procedures section of this specification. The solid bar identifies the coding region, and the fine line represents the 5' and 3' untranslated regions. SP6, T3 and T7 refer to the SP6, T3 and T7 transcription promoters.

FIG. 2 is a photograph showing an analysis by in situ hybridization histochemistry of the distribution of β4 transcripts. Adult rat brain coronal sections (30 μm thick) were hybridized with $^{35}S$-radiolabeled sense and antisense strands probes derived from KpnI- and BamHI-linearized pGDD15, respectively (see FIG. 1C).

FIGS. 3-1 through 3-5 is a schematic drawing showing the nucleotide sequence and deduced amino acid sequence of λZPC13. The genomic nucleotide sequences at the splice junctions and at the substitution position (720) are shown above the cDNA sequence in lowercase letters. Vertical bars indicate the predicted splice sites. The core position of a DNA sequence repeated three times is boxed in gray. Putative membrane spanning regions (MSRs) are indicated. The polyadenylation signal is underlined. A scissors indicates predicted signal peptide cleavage site. An asterisk indicates putative N-linked glycosylation sites.

FIGS. 4-1 and 4-2 is a schematic drawing showing amino acid alignment of the rat neuronal β-type subunits. Aligned with the β4 subunit are the β2 (U.S. Ser. Nos. 170,295 and 321,384 and Deneris, et al., 1988) and β3 (U.S. Ser. Nos. 170,295 and 321,384 and Deneris, et al., 1989) sequences. Identical residues in all three subunits are shown on a black background. Conservative changes are indicated by a gray background. Putative signal peptides and membrane spanning regions are identified below the sequences. The region referred to as the extracellular domain is located between the amino terminus and MSR I, and the putative cytoplasmic domain is located between MSR III and MSR IV. The numbering is that of the precursor β4 subunit.

FIGS. 6A and 6B shows voltage recordings of Xenopus oocytes injected with α3 and either β2 or β4 before and after exposure to ~0.1 μM 3.1 Bgt. Representative responses induced by acetylcholine and nicotine stimulations at the given concentrations are shown. Potential measurements were monitored on a digital voltmeter and recorded on a Gould pen recorder. Voltage traces were scanned and prepared for printing using a personal computer.

DEFINITIONS

Figure 2B:
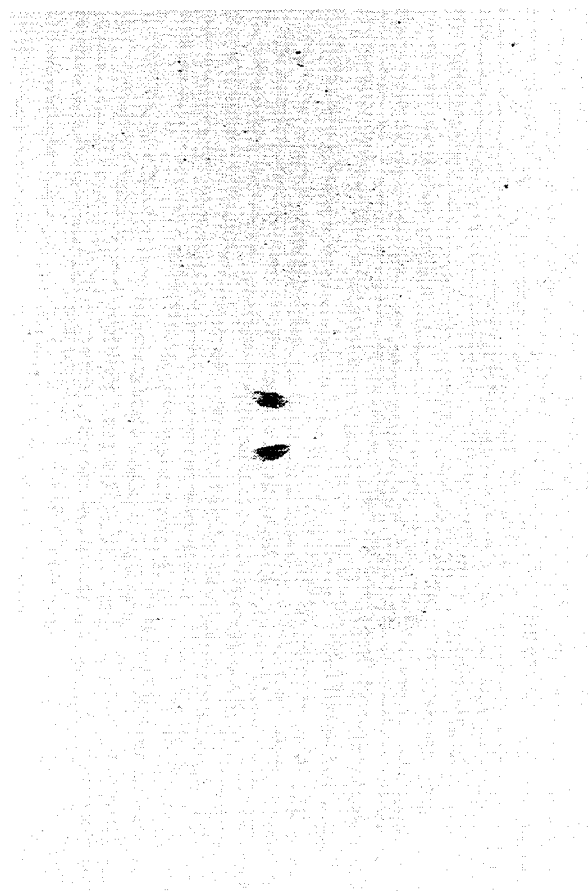
FIG. 2B is a dark-field photomicrograph of a medial habenula form a section identical to that shown in FIG. 2A after emulsion dipping.

In the present specification and claims, reference will be made to phrases and terms of art which are expressly defined for use herein as follows:

As used herein, nAChR means nicotinic acetylcholine receptor.

As used herein, an agonist binding subunit is a subunit of an acetylcholine receptor that contains a binding site for the neurotransmitter, acetylcholine and its analogs.

A putative neuronal nAChR subunit isolated by cDNA cloning is identified as an "alpha" (α) subunit if the Torpedo alpha subunit cysteines 128, 142, 192, and 193 are conserved. Some alpha subunits are known to be agonist binding subunits, others are suspected of being agonist binding subunits based on the fact that they contain the conserved cysteines at positions 128, 142, 192, and 193. Known α-type agonist binding subunits include alpha1, and alpha4 (alpha4.1 and alpha4.2); suspected α-type agonist binding subunits include alpha2, alpha3, and alpha5.

A putative neuronal nAChR subunit isolated by cDNA cloning is identified as a "beta" (β) subunit if only the Torpedo 128 and 142 cysteines are conserved. Known β-subunits include beta1, beta2 and beta3. The novel beta subunit of the invention is beta4.

As used herein, the term antagonist refers to a substance that interferes with receptor function. Antagonists are of two types: competitive and non-competitive. A competitive antagonist (or competitive blocker) competes with the neurotransmitter for the same binding site. In the case of acetylcholine, an example of such an antagonist is 3.1 bungarotoxin. A non-competitive antagonist or blocker inactivates the functioning of the receptor by binding to a site other than the acetylcholine binding site.

As used herein, alpha1 refers to a DNA segment which encodes an agonist binding subunit of the same name. This subunit is expressed in skeletal muscle and Torpedo electric organ.

As used herein, alpha2 refers to a DNA segment, which has been identified in chick and rat, that encodes a neuronal nAChR subunit of the same name. DNA encoding the alpha2 subunit has been deposited with the ATCC; the DNA (designated as pHYP16) has been accorded ATCC No. 67646.

As used herein, alpha3 refers to a DNA segment that encodes a neuronal nAChR subunit of the same name. This subunit is expressed in the PC12 cell line and various regions of the mammalian brain. DNA encoding the alpha3 subunit has been deposited with the ATCC; the DNA (designated as pPCA48) has been accorded ATCC No. 67642.

As used herein, alpha4 refers to a DNA segment that encodes a neuronal agonist binding subunit of the same name. The cDNA clones encoding the proteins referred to herein as alpha4.1 and 4.2 are both derived from the alpha4 gene. DNAs coding for the alpha4.1 and 4.2 trancripts have been deposited with the ATCC. The alpha4.1 DNA (designated as pHYA23-1(E)1) has been accorded ATCC No. 67644; the alpha4.2 DNA (designated as pHIP3C(3) has been accorded ATCC No. 67645.

As used herein, alpha5 refers to a DNA segment encoding a neuronal nAChR subunit of the same name. DNA encoding the alpha5 subunit has been deposited with the ATCC; the DNA (designated as PC1321) has been accorded ATCC No. 67652.

As used herein, beta1 refers to a DNA segment encoding a nAChR subunit of the same name. This subunit is expressed in the Torpedo electric organ and mammalian muscle receptors.

As used herein, beta2 refers to a DNA segment encoding a neuronal nAChR subunit of the same name. See U.S. Ser. Nos. 07/170,295, abandoned and 07/321,384, abandoned, and Deneris, et al., (1988). DNA encoding beta2 has been deposited with the ATCC; the DNA (designated as pPCX49) has been accorded ATCC No. 67643.

As used herein, beta3 refers to a DNA segment encoding a neuronal nAChR subunit of the same name. See U.S. Ser. Nos. 07/170,295, abandoned and 07/321,384, abandoned, and Deneris, et al., (1989). DNA encoding beta3 has been deposited with the ATCC; the DNA (designated as EDS76) has been accorded ATCC No. 67653.

As used herein, beta4 refers to a DNA segment encoding a neuronal nAChR subunit of the same name. DNA encoding the beta4 subunit has been deposited with the ATCC; the DNA (designated as pZPC13) has been accorded ATCC No. 67893.

As used herein, PC12 refers to the rat adrenal chromaffin tumor cell line, PC12. This cell line expresses presses a "ganglionic" nicotinic acetylcholine receptor of the type found in sympathetic neurons.

Use of the phrase "substantial sequence homology" in the present specification and claims means that DNA, RNA or amino acid sequences which have slight and non-consequential sequence variations from the actual sequences disclosed and claimed herein are considered to be equivalent to the sequences of the present invention, and as such are within the scope of the appended claims. In this regard, "slight and non-consequential sequence variations" mean that "homologous" sequences (i.e., the sequences that have substantial sequence homology with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

Use of the phrase "substantially pure" in the present specification and claims as a modifier of DNA, RNA, polypeptides or proteins means that the DNA, RNA, polypeptides or proteins so designated have been separated from their in vivo cellular environments through the efforts of human beings; as a result of this separation, the substantially pure DNAs, RNAs, polypeptides and proteins are useful in ways that the non-separated, impure DNAs, RNAs, polypeptides or proteins are not.

The amino acids which comprise the various amino acid sequences appearing herein may be identified according to the following three-letter or one-letter abbreviations:

| Amino Acid | 3 Letter Abbreviation | 1 Letter Abbreviation |
| --- | --- | --- |
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

The nucleotides which comprise the various nucleotide sequences appearing herein have their usual single-letter designations (A, G, T, C or U) used routinely in the art.

In present specification and claims, references to Greek letters are written as both as alpha, beta, gamma, delta, epsilon, etc., and as α, μ, γ, δ, ε, etc.

In the present specification, temperatures are in degrees Centigrade unless specified otherwise.

DEPOSITS cDNA clones comprising neuronal nicotinic acetylcholine receptor subunits alpha2 (clone pHYP16), alpha3 (clone pPCA48), alpha4.1 (clone pHYA23-1(E)1), alpha4.2 (clone pHIP3C(E)3), alpha5 (clone PC1321), beta2 (clone pPCX49), beta3 (clone EDS76) and beta4 (clone pZPC13), all of which are in E. coli HB101, have been deposited at the American Type Culture Collection, Rockville, Md., U.S.A. (ATCC) under the terms of the Budapest Treaty on the International Recognition of Deposits of Microorganisms for Purposes of Patent Procedure and the Regulations promulgated under this Treaty. Samples of the cloned subunits are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this application, is filed or in which any patent granted on any such application is granted.

The ATCC Deposit Numbers for the various deposits are as follows:

| | | |
|---|---|---|
| alpha2 | clone pHYP16 | ATCC No. 67646 |
| alpha3 | clone pPCA48 | ATCC No. 67642 |
| alpha4.1 | clone pHYA23-1(E)1 | ATCC No. 67644 |
| alpha4.2 | clone pHIP3C(3) | ATCC No. 67645 |
| alpha5 | clone PC1321 | ATCC No. 67652 |
| beta2 | clone pPCX49 | ATCC No. 67643 |
| beta3 | clone EDS76 | ATCC No. 67653 |
| beta4 | clone pZPC13 | ATCC No. 67893 |

SUMMARY OF THE INVENTION

The invention discloses a new subunit member of the family of mammalian neuronal nicotinic acetylcholine receptors. The new subunit, named β4, can combine with known subunits, including α-type subunits α2, α3 and α4, and the β-type subunit, β2, in the presence of at least one alpha, to form previously unknown functional receptors.

More specifically, in one aspect, the present invention is a substantially pure functional neuronal nicotinic acetylcholine receptor comprised of at least one beta4 subunit.

In another aspect, the present invention is a substantially pure functional neuronal nicotinic acetylcholine receptor comprised of at least one beta4 subunit and at least one non-beta4 subunit wherein at least one of the non-beta4 subunits will be an alpha subunit.

In another aspect, the invention is a substantially pure neuronal nicotinic acetylcholine receptor subunit, beta4.

In another aspect, the invention is a DNA segment comprising substantially pure double-stranded DNA sequences wherein the sense strand encodes the amino acid sequence of the mammalian neuronal nicotinic acetylcholine receptor subunit, beta4.

In another aspect, the invention comprises substantially pure single-stranded DNA and mRNA transcribed therefrom wherein the sequences encode the amino acid sequence of the mammalian neuronal nicotinic acetylcholine receptor subunit, beta4.

In another aspect, the invention comprises substantially pure DNA sequences encoding the neuronal nicotinic acetylcholine receptor beta4 subunit of the present invention. A cDNA clone comprised of such sequences has been deposited with the American Type Culture Collection for patent purposes. The cDNA of the invention is identified as beta4 (clone pZPC13, ATCC No. 67893). DNA sequences from the clone can be used as probes to identify and isolate other neuronal nicotinic acetylcholine receptors from cDNA libraries.

In still another aspect, the invention comprises a cell, preferably a mammalian cell, transfected with DNA sequences of the invention.

Still further, the invention comprises novel neuronal nicotinic acetylcholine receptors made by expression of DNA sequences of the invention, or translation of the corresponding mRNAs. Such novel receptors include receptors that contain only the beta4 subunit, plus functional combinations that contain at least one beta4 subunit and at least one other non-beta4 subunit. Functional combinations of the present invention include, but are not limited to, receptors that contain: at least one beta4 subunit and at least one alpha2 subunit; at least one beta4 subunit and at least one alpha3 subunit; at least one beta4 subunit and at least one alpha4; and at least one beta4 subunit, at least one beta2, and at least one alpha subunit.

Still further the invention comprises DNA, RNA and proteins that are functionally equivalent to the DNAs, RNAs and proteins of the present invention. Such functionally equivalent DNAs, RNAs and proteins will function in substantially the same manner as the DNAs, RNAs and proteins of the invention.

In yet another aspect, the invention comprises use of substantially pure functional neuronal nicotinic acetylcholine receptors, comprised of at least one beta4 subunit, to screen for neuronal nicotinic acetylcholine receptor agonists and antagonists.

DETAILED DESCRIPTION OF THE INVENTION

The present invention is the discovery and isolation of DNA segments that encode a new neuronal nicotinic receptor subunit, beta4 (β4). The new subunit is expressed in the central and peripheral nervous systems and in PC12 cells, and can participate in the formation of functional nAChRs with previously described alpha (α) and beta (β) subunits.

To gain access to the new neuronal receptor subunit, mammalian (rat) genomic libraries were screened with neuronal nAChR probes. A recombinant phage containing DNA sequences encoding a novel nAChR subunit was isolated. The primary structure of this subunit was deduced from the nucleotide sequence of a cDNA clone. Expression studies using Xenopus oocytes showed that this subunit can combine with each of the neuronal α2, α3, α4 subunits, and the β2 subunit, in combination with at least one alpha subunit, to form functional nAChRs.

As the results in the following Examples demonstrate, the beta4 subunit is expressed in the mammalian central and peripheral nervous systems. The results also show that β4 subunit is most related to the β2 subunit (64% overall amino acid sequence identity) and closely resembles the other neuronal nicotinic receptor subunits cloned in our Molecular Neurobiology Laboratory at the Salk Institute for Biological Studies (48% identity with α2, 46% with α3, 52% with α4, and 44% with β3). Expression studies reveal that at least four different types of functional neuronal nicotinic acetylcholine receptors are produced upon co-injection into oocytes of beta4 mRNAs and each of the neuronal alpha2, alpha3, alpha4 and beta2 mRNAs. See Example 4.

As those skilled in the art will know, ganglionic nAChRs are blocked by bungarotoxin 3.1 (3.1 Bgt). In oocytes, nAChRs comprised of the rat α3 or α4 subunit in combination with the β2 subunit are blocked by this toxin (see U.S. Ser. Nos. 07/170,295, abandoned and 07/321,384, abandoned, and Boulter, et al., 1987); the α4β2 combination is much less sensitive than the α3β2 combination (Luetje, et al., 1990). Receptors comprised of the α2 and β2 subunits are not blocked by 3.1 Bgt (see U.S. Ser. Nos. 07/170,295, abandoned and 07/321,384, abandoned, and Wada, et al., 1988). As the results in Example 4 demonstrate, surprisingly, the α3β4 combination is not blocked by the toxin. This result suggests a participation of the β subunit in the effect of 3.1 Bgt on neuronal nicotinic receptors.

A representative cDNA clone that encodes the new neuronal nicotinic acetylcholine receptor subunit of the present invention has been deposited with the ATCC for patent purposes. This beta4 DNA has been accorded ATCC No. 67893. The DNA and amino acid sequences for beta4 are shown in FIG. 3.

Without further elaboration, it is believed that one of ordinary skill in the art can, using the preceding description, and the following Examples and Experimental Procedures sections, utilize the present invention to its fullest extent. The material disclosed in the Examples and the Experimental Procedures section, unless otherwise indicated, is disclosed for illustrative purposes and therefore should not be construed as being limiting in any way of the appended claims.

EXAMPLES AND EXPERIMENTAL PROCEDURES

EXAMPLE 1

Identification of a New nAChR Gene

To isolate previously unidentified nAChR subunits, rat genomic libraries were screened with neuronal nicotinic receptor cDNA probes. A genomic library (Sierra, et al., 1986) constructed in the replacement vector EMBL3 was screened with a β2 cDNA probe, and four independent recombinant phage were isolated. Three clones were shown to be overlapping and contained the β2 gene. The restriction map of the fourth clone, λDD15 (FIG. 1A), was incompatible with that of the β2 gene. To determine unambiguously that this clone contained the gene for an unidentified nAChR subunit, the nucleotide sequence of a small fragment (AluI-AluI [710–1149]; see FIG. 3), which hybridized to the β2 probe, was determined. The deduced amino acid sequence was related to, but different from, that of β2 and other cloned nAChR subunits.

The α subunit of nAChRs contains two adjacent cysteine residues (192 and 193 in the Torpedo electric organ α subunit; Noda, et al., 1982), which are believed to be close to the ligand binding domain of the receptor (Kao, et al., 1984). In sequenced neuronal nAChRs genes, this region is encoded by the fifth exon (Nef, et al., 1988). As indicated in the Definitions section of this specification, when functional studies are not available, the presence or absence of these cysteine residues is used to classify a subunit into the α or β type, respectively. In addition, the fifth exon encodes most of the postulated cytoplasmic domain of each subunit. Primary structure comparisons between the different nAChR subunits reveals a low conservation of this protein domain, and DNA fragments encoding this region can therefore be used as subunit-specific probes. The nucleotide sequence of the fifth exon of the gene encoded by λDD15 was determined (FIG. 1B; also see, FIG. 3). Since the deduced amino acid sequence does not contain the adjacent cysteine residues, this subunit was named β4; β1 is a muscle subunit and β2 and β3 are two previously discovered β-type neuronal subunits (see U.S. Ser. Nos. 07/170,295, abandoned and 07/321,384, abandoned, and Deneris, et al., 1988, 1989).

EXAMPLE 2

The β4 Gene Is Expressed in The Rat Nervous System

Figure 2A:
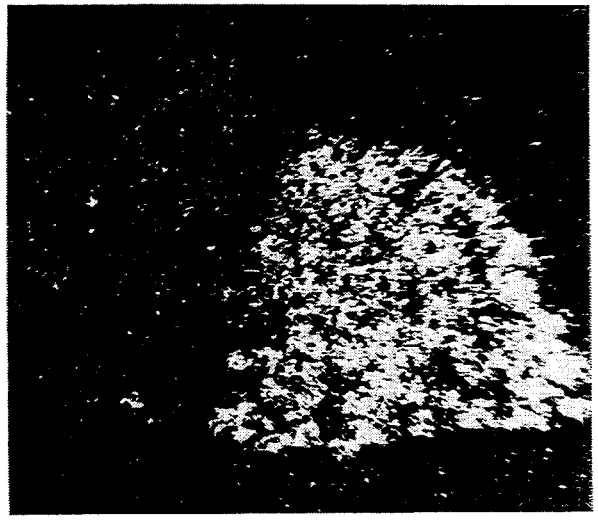
FIG. 2A shows that only sections across the thalamus, as the one shown here, gave above background signals by X-ray film autoradiography. In parallel experiments, a sense probe was hybridized to adjacent sections and gave background levels of hybridization (data not shown).
Figure 5A:
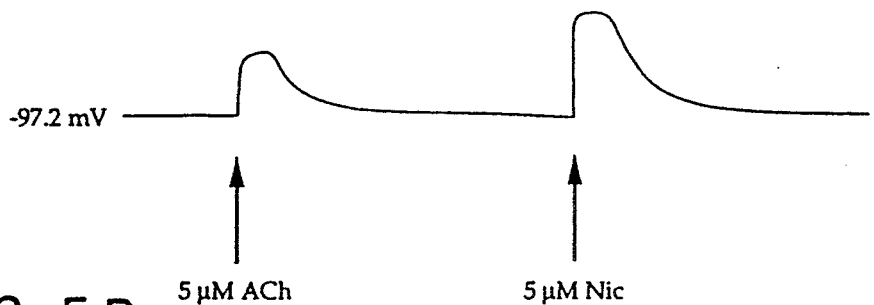
FIGS. 5A through 5D shows electrophysiological recordings of Xenopus oocytes injected with in vitro synthesized RNA encoding the nAChR subunits in the indicated combinations. Representative responses induced by acetylcholine and nicotine stimulations at the given concentrations are shown. Potential measurements were monitored on a digital voltmeter and recorded on a Gould pen recorder. Voltage traces were scanned and prepared for printing using a personal computer.
Figure 5B:
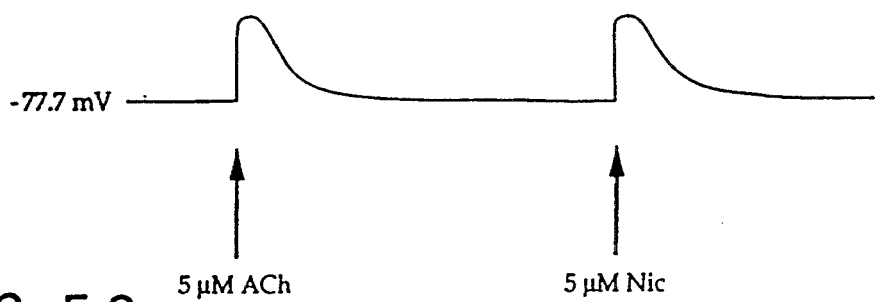
Figure 5C:
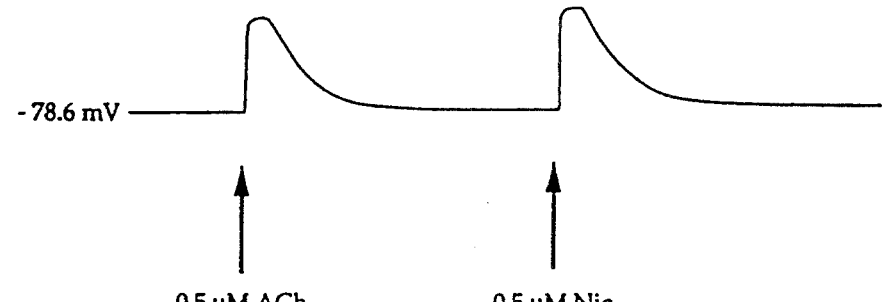
Figure 5D:
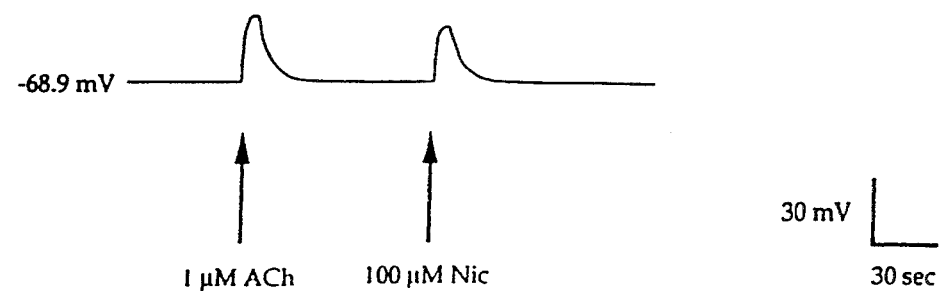

In situ hybridization histochemistry of adult rat brain sections was performed to determine whether the β4 gene is expressed in the central nervous system. To synthesize β4-specific RNA probes, the plasmid pGDD15 was constructed by inserting a genomic DNA fragment encoding a nonconserved part of the cytoplasmic domain into a plasmid vector (FIG. 1C). The insert is located between the transcription initiation sites for SP6 and T7 RNA polymerases, allowing the in vitro transcription of sense or antisense RNA probes. FIG. 2A shows an autoradiograph of a rat brain coronal section at the level of the thalamus using a $^{35}$S-radiolabeled antisense probe. The medial habenula is the only region where above background hybridization was detected by X-ray film autoradiography. Furthermore, as shown in FIG. 2B, β4 transcripts are highly localized to the ventral two-thirds of the medial habenula. However, a few cells in the dorsal medial habenula may also contain lower levels of β4 mRNA. This result is in contrast with the pervasive distribution of the α3, α4, and β2 transcripts in the rat brain (U.S. Ser. Nos. 07/170,295, abandoned and 07/321,384, abandoned, and Goldman, et al., 1986, 1987; Deneris, et al., 1988; Wada, et al., 1989).

Since the pheochromocytoma cell line PC12 has been shown to express nicotinic receptors and several cDNA clones encoding nAChR subunits were isolated from PC12 cDNA libraries, tests were run to determine whether this cell line might provide an abundant source of β4 transcripts. RNAase protection experiments revealed β4 gene expression in these cells (data not shown). Furthermore, β4 mRNA was also found in rat adrenal gland poly(A)+ RNA, indicating expression of the β4 gene in the peripheral nervous system (Boulter, et al., unpublished data).

EXAMPLE 3

Primary Structure of β4

Verification that the β4 gene did indeed encode a novel nAChR subunit required functional expression. For this purpose, and to determine the primary structure of the β4 subunit, cDNA clones were isolated. Double-stranded cDNA was prepared and inserted unidirectionally between the EcoRI and XhoI sites of the λ phage vector λZAPII. The screening of $1 \times 10^6$ phage with a β4 riboprobe resulted in the identification of 8 clones, which were purified. The cDNA insert of these clones was transferred from the λ phage vector into a plasmid by the in vivo excision procedure (Short, et al., 1988), and the 5'end nucleotide sequence of six inserts was determined. The insert of pZPC13 (the plasmid analog of λZPC13) was sequenced and shown to contain the entire coding sequence of β4 and a complete 3' untranslated region (FIG. 1D; FIG. 3). The sequence of the cDNA in the region encoded by the fifth exon is identical to that determined from the genomic clone with the exception of a substitution of a T for a C at position 720 (FIG. 3). This difference does not alter the deduced amino acid sequence. It could be due to a polymorphism between the rat strain that served as a source of the PC12 cell line and the rat strain from which a genomic library was prepared. Alternatively, it could result from a cDNA cloning artifact, such as a reverse transcriptase error. A sequence, the core of which is 44 bp long, is repeated three times at the beginning of the 3' untranslated region (FIG. 3, gray boxes). This sequence probably did not arise by a cloning artifact, since another clone, pZPC11, contains the same direct repeats. A search of the EMBO database (release 17) did not reveal another occurrence of this sequence, and the function, if any, of this repeat remains to be investigated.

The open reading frame of pZPC13, from the first ATG, which lies in a favorable context for translation initiation (Kozak, 1986), to the TGA termination codon at position 1546, encodes a protein of 495 residues. Analysis of the deduced amino acid sequence reveals features characteristic of a ligand-gated ion channel subunit, including four putative transmembrane domains, found using the algorithm of Eisenberg, et al. (1984). The β4 subunit is most related to the β2 subunit (64% overall amino acid sequence identity) and closely resembles the other rat neuronal nicotinic receptor subunits cloned in the Molecular Neurobiology Laboratory at the Salk Institute for Biological Studies (48% identity with α2, 46% with α3, 52% with α4, and 44% with β3). The amino-terminal residues are characteristic of a signal peptide, but the method of von Heijne (1986) does not predict an unambiguous cleavage site; the highest score suggesting a cleavage site between positions 20 and 21. Since it was not possible to conclusively determine the amino terminal residue of the mature protein, the numbering used throughout this specification refers to the precursor protein. As shown in FIG. 4, which presents an amino acid alignment of the neuronal β subunits, the predicted membrane spanning regions I through III are highly conserved. The extracellular domain, the fourth membrane spanning region, and about 30 residues at each end of the cytoplasmic domain also exhibit conserved residues. All three β subunits contain the characteristic 2 cysteine residues corresponding to residues 128 and 142 of the Torpedo electric organ α subunit (Noda, et al., 1982: β4 subunit positions 152 and 166 in FIGS. 3 and 4), but not the 2 adjacent cysteines characteristic of α-type subunits. The extracellular domain of neuronal nAChR subunits have two potential N-linked glycosylation sites. The β4 subunit is distinctive in having four such sites; one is at the conserved residue position 165, another is at position 35, and the two additional glycosylation sites are located at residues 92 and 137. Of the three neuronal β-type subunits, β4 has the longest cytoplasmic domain.

EXAMPLE 4

The β4 Subunit Combines with the α2, α3, and α4 Subunits to Form Functional nAChRs The deduced primary structure of the λZPC13 encoded protein suggests that it is a β-type subunit of the neuronal nicotinic receptors. To test this hypothesis, expression studies in Xenopus oocytes were undertaken. Pairwise injections of oocytes with in vitro synthesized RNA encoding the β4 subunit and either the α2, α3, or α4 subunit were performed. Upon bath application of acetylcholine or nicotine, oocytes injected with each combination were depolarized; examples of such voltage responses are given in FIG. 5. These results are similar to those previously reported for the α2β2, α3β2, and β4β2 combinations (see U.S. Ser. Nos. 07/170,295, abandoned, and 07/321,384, abandoned; Boulter, et al., 1987; Wada, et al., 1988) and demonstrate that β4 is a novel, functional nicotinic receptor subunit. Injection of the β4 RNA alone (n=8) and β4 in combination with β2 (n=6) failed to produce responses upon stimulation with up to 1 mM acetylcholine (data not shown). Taken together, these results indicate that the β4 subunit is functionally equivalent to the β2 subunit. Furthermore, this supports assigning an α or β designation to neuronal nAChR subunits based upon the occurrence of paired cysteine residues in the extracellular domain.

Since the β2 subunit functionally substitutes for the muscle β1 subunit (Deneris, et al., 1988), tests were run to determine whether the β4 subunit could also be combined with the muscle α1, γ, and δ subunits to form a functional receptor. Parallel experiments in which oocytes were injected with either the α1γε or the α1β4γδ RNA combinations were performed. Oocytes injected with the α1Δδ combination gave no response to the application of 1 μM acetylcholine (n=9, average resting potential=−69 mV), although, as previously shown (Kurosaki, et al., 1987), higher concentrations of acetylcholine do elicit small responses (11±8 m depolarizations at 1 mM, n=5). On the other hand, oocytes injected with the α1β4γδ combination gave an average depolarization of 43±25 mV when challenged with 1 μM acetylcholine (n=5; FIG. 5). Thus, the inclusion of the β4 subunit RNA restores strong functional expression to the muscle α1γδ combination. Injection of only α1 and β4 RNA did not yield functional receptors (n=9), confirming the observation that γ or δ subunits are required in combination with the muscle α1 subunit for the formation of functional nAChRs (Kurosaki, et al., 1987).

Ganglionic nAChRs are blocked by bungarotoxin 3.1 (3.1 Bgt; also referred to as neuronal bungarotoxin by Lindstrom, et al., (1987); toxin F by Loring, et al., (1984); and κ-bungarotoxin by Chiappinelli, (1983). In oocytes, nAChRs comprised of the rat α3 or α4 subunit in combination with the β2 subunit are blocked by this toxin (Boulter, et al., 1987), although the α4β2 combination is much less sensitive than the α3β2 combination (Luetje, et al., 1990). Receptors comprised of the α2 and β2 subunits are not blocked by 3.1 Bgt (Wada, et al., 1988). To test the effect of substituting the β-type subunits, comparisons were made of the 3.1 Bgt block of acetylcholine responses in oocytes injected with the α3β2 and α3β4 combinations. As expected, 3.1 Bgt blocked the activity of the α3β2 receptor in response to 1 μM acetylcholine applications (FIG. 6). In parallel experiments, the β3β4 combination was not blocked by the toxin. This result suggests a participation of the β subunit in the effect of 3.1 Bgt on neuronal nicotinic receptors.

EXAMPLE 5

Use of nAChRs to Screen for nAChR Agonists and Antagonists

Functional neuronal nicotinic acetylcholine receptors can be used to screen for nAChR agonists and antagonists. In one preferred method, functional neuronal nicotinic acetylcholine receptors, comprised of functional combinations of the alpha2, alpha3, alpha4, beta2 and beta4 subunits, are created by transfecting suitable cells (e.g., cultured fibroblasts or neuronal cells) with DNA encoding the various alpha and beta subunits. Known electrophysiological methods are then used to determine the effect of known and potential agonists and antagonists on the transfected cells. Such methods include, but are not limited to, depolarizations and current recordings under a voltage clamp.

A second preferred method for screening for known and potential nAChR agonists and antagonists utilizes conventional binding assays wherein the transfected cells are contacted with labeled agonists or antagonists. Appropriate labels include radio labels, fluorescent labels and the like. This type of assay allows the measurement of binding as well as displacement of bound agonists or antagonists.

EXPERIMENTAL PROCEDURES

Screening of Genomic Libraries

The library, from which the λXDD15 clone was isolated, was constructed in the λ phage vector EMBL3 (Sierra et al., 1986). Approximately $10^6$ phage were screened with a PCX49 (Deneris et al., 1988) probe $^{32}$P-labeled by random priming (Multi-prime, Amersham, Arlington Heights, Ill.). The filters were hybridized overnight at 65° C. in 5×SSPE, 1% SDS, 1×Denhardt's solution. Washes were for 30 min at 65° C., twice in 2×SSC, 1% SDS and once in 0.2×SSC, 1% SDS. SSPE, Denhardt's solution, and SSC were as defined by Maniatis, et al. (1982).

In Situ Hybridization

To prepare β4-specific probes, the plasmid pGDD15 was constructed by inserting the approximately 450 bp fragment from an NcoI site (FIG. 3, position 1040) to the SalI site in the EMBL3 linker into the SmaI site of the pGEM-3Z expression vector (Promega, Madison, Wis.) after Klenow filling-in of the protruding ends (see FIG. 1). Using SP6 or T7 RNA polymerase, $^{35}$S-labeled sense or antisense RNA probes were synthesized in vitro from KpnI- or BamHI-linearized pGDD15. Conditions for in situ hybridization histochemistry were as previously described (U.S. Ser. Nos. 07/170,295, abandoned, and 07/321,384, abandoned, and Deneris, et al., 1988).

Construction and Screening of the cDNA Library

Total RNA was extracted from PC12 cells according to Cathala, et al., (1983). Poly(A)+ RNA was prepared batchwise using oligo(dT) Sepharose fines (Pharmacia, Piscataway, N.J.) as described (Nagamine et al., 1983). Five micrograms was used to construct a directional cDNA library in λZAPII using the UniZAP kit (Stratagene, San Diego, Calif.). Yields were approximately $5 \times 10^6$ recombinant phage per μg of RNA. Approximately $10^6$ phage were screened with a $^{32}$P-labeled RNA probe derived from pGDD15. Filters were hybridized overnight at 42° C. in 50% formamide, 5×SSPE, 0.5% SDS and washed several times at increasing stringencies. The final washing was performed at 75° C. in 0.1×SSC, 0.1% SDS. The cDNA inserts were transferred into plasmid vectors by the in vivo excision protocol (Short, et al., 1988). Briefly, recombinant λ phage stocks were used with R408 f1 helper phage to coinfect exponential cultures of the XL1-blue strain of E. coli. Cultures were grown for 6 hr at 37° C. and centrifuged at 7000×g for 10 min. Samples of the culture supernatants were used to infect XL1-blue bacteria, which were plated out on L-agar plates containing 100 μg/ml ampicillin. Resistant colonies contain the cDNA insert in the plasmid vector pBluescript SK(−) (Stratagene, San Diego, Calif.).

Nucleotide Sequence Determination and Analysis

Appropriate restriction fragments were subcloned into the single stranded phage vectors M13mp18 and M13mp19 (Yanish-Perron, et al., 1985). The nucleotide sequence of the inserts was determined using the Sequenase kit (United States Biochemicals, Cleveland, Ohio) and either the universal primer supplied or oligonucleotides synthesized on a Cyclone DNA synthesizer (Biosearch, San Rafael, Calif.). Sequence analysis was facilitated by the use of the PC/GENE (Genofit SA, Geneva, Switzerland) and UW-GCG (Devereux, et al., 1984) software packages. Deduced amino acid sequences were aligned with each other. The percentage of sequence identity between subunits was calculated by dividing the number of identical residues by the number of residues compared (thus excluding gaps from the calculation). Similar amino acids were defined as follows: A, S, T; D, E; N, Q; R, K; I, L, M, V; F, Y, W.

Expression in Xenopus oocytes and Electrophysiology

RNA was synthesized in vitro using linearized template DNA encoding α2 (U.S. Ser. Nos. 07/170,295, abandoned, and 07/321,384, abandoned, and Wada, et al., 1988), α3, α4, and β2 as previously described (U.S. Ser. Nos. 07/170,295, abandoned, and 07/321,384, abandoned, and Boulter, et al., 1987). Diguanosine triphosphate-capped β4 encoding RNA was prepared similarly from XhoI-linearized pZPC13 template DNA using T3 RNA polymerase (Stratagene, San Diego, Calif.).

Oocytes were taken from anesthetized, mature female Xenopus (Xenopus I, Madison, Wis.), and follicle cells were removed by treatment with collagenase type IA (Sigma Chemical Co., St. Louis, Mo.) for 2 hr at room temperature with continuous slow agitation. Each oocyte was injected with approximately 5 ng of RNA in a volume of 50 nl of water and incubated in Barth's saline (Coleman, 1984) at 20° C. for 2 days. Alternatively, transfection can be accomplished with corresponding DNA sequences.

Electrophysiological recordings were performed as previously described (U.S. Ser. Nos. 07/170,295, abandoned, and 07/321,384, abandoned, and Boulter, et al., 1987). 3.1 Bgt was prepared according to Ravdin and Berg (1979). Several recordings were made using an independently purified preparation of 3.1 Bgt sample with the same results.

REFERENCES

The following references have been cited in the present specification. All cited references are expressly incorporated by reference herein.

1. Barnard, E. A., Darlison, M. G., and Seeburg, P. (1987). Molecular biology of the $GABA_A$ receptor: the receptor/channel superfamily. Trends Neurosci. 10, 502–509.
2. Bormann, J., and Matthaei, H. (1983). Three types of acetylcholine-induced single channel currents in clonal rat pheochromocytoma cells. *Neurosci. Lett.* 40, 193-197.
3. Boulter, J., Evans, K., Goldman, D., Martin, G., Treco, D., Heinemann, S., and Patrick, J. (1986). Isolation of a cDNA clone coding for a possible neural nicotinic acetylcholine receptor alpha-subunit. *Nature* 319 368-374.
4. Boulter, J., Connolly, J., Deneris, E., Goldman, D., Heinemann, S., and Patrick, J. (1987). Functional expresion of two neural nicotinic acetylcholine receptors from cDNA clones identifies a gene family. *Proc. Natl. Acad. Sci. USA* 84, 7763-7767.
5. Boulter, J., O'Shea-Greenfield, A., Duvoisin, R., Connolly, J., Wada, E., Jensen, A., Gardner, P., Ballivet, Deneris, E., McKinnon, D., Heinemann, S., and Patrick, J. (1990). $\alpha 3$, $\alpha 5$ and $\beta 4$: Three Members of the Rat Neuronal Nicotinic Acetylcholine Receptor-related Gene Family Form a Gene Cluster. *J. Biol. Chem.* 265, 4472-4482.
6. Cathala, G., Savouret, J., Mendez, B., West, B., Karin, M., Martial J., and Baxter, J. (1983). A method for isolation of intact, translationally active ribonucleic acid. *DNA* 2, 329-335.
7. Changeux, J. (1981). The acetylcholine receptor: an "allosteric" membrane protein. *Harvey Lect.* 75, 85-254.
8. Chiappinelli, V. A. (1983). Kappa-bungarotoxin: a probe for the neuronal nicotinic receptor in the avian ciliary ganglion. *Brain Res.* 277, 9-21.
9. Coleman, A. (1984). Translation of eukaryotic messenger RNA in Xenopus oocytes. In *Transcription and Translation: A Practical Approach*. B. D. Hames and S. J. Higgins, eds. (Oxford: IRL Press Ltd.), pp. 271-302.
10. Deneris, E. S., Connolly, J., Boulter, J., Wada, E., Wada, K., Swanson, L. W., Patrick, J., and Heinemann, S. (1988). Primary structure and expression of $\beta 2$: a novel subunit of neuronal nicotinic acetylcholine receptors. *Neuron* 1, 45-54.
11. Deneris, E. S., Boulter, J., Swanson, L. W., Patrick, J., and Heinemann, S. (1989). $\beta 3$: a new member of nicotinic acetylcholine receptor gene family is expressed in brain. *J. Biol. Chem.* 264, 6268-6272.
12. Devereux, J., Haeberli, P., and Smithies, O. (1984). A comprehensive set of sequence analysis programs for the VAX. *Nucl. Acids Res.* 12, 387-395.
13. Eisenberg, D., Schwartz, E., Komaromy, M., and Wall, R. (1984). Analysis of membrane and surface protein sequences with the hydrophobic moment plot. *J. Mol. Biol.* 179, 125-142.
14. Goldman, D., Simmons, D., Swanson, L. W., Patrick, J., and Heinemann, S. (1986). Mapping of brain areas expressing RNA homologous to two different acetylcholine receptor $\alpha$-subunit cDNAs. *Proc. Natl. Acad. Sci. USA* 83, 4076-4080.
15. Goldman, D., Deneris, E, Lutyten, W., Kochhar, A., Patrick, J. and Heinemann, S. (1987). Members of a nicotinic acetylcholine receptor gene family are expressed in different regions of the mammalian central nervous system. *Cell* 48, 965-973.
16. Gu, Y., and Hall, Z. W. (1988). Immunological evidence for a change in subunits of the acetylcholine receptor in developing and denervated rat muscle. *Neuron* 1, 117-125.
17. Hall, Z. W. (1987). Three of a kind: the $\beta$-adrenergic receptor, the muscarinic acetylcholine receptor, and rhodopsin. *Trends Neurosci.* 10, 99-101.
18. Halvorsen, S. W., and Berg, D. K. (1987). Affinity labeling of neuronal acetylcholine receptor subunits with an $\alpha$-neurotoxin that blocks receptor function. *J. Neurosci.* 7, 2547-2555.
19. Isenberg, K. E., and Meyer, G. E. (1989). Cloning of a putative neuronal nicotinic acetylcholine receptor subunit. *J. Neurochem.* 52, 988-991.
20. Kao, P. N., Dwork, A. J., Kaldany, R. J., Silver, M. L., Wideman, J., Stein, S., and Karlin, A. (1984). Identification of two alpha-subunit half-cystines specifically labeled by an affinity reagent for the acetylcholine binding site. *J. Biol. Chem.* 259, 1162-1165.
21. Kozak, M. (1986). Point mutations define a sequence flanking the AUG initiator codon that modulates translation by eukaryotic ribosomes. *Cell* 44, 283-292.
22. Kurosaki, T., Fukuda, K., Konno, T., Mori, Y., Tanaka, K., Mishina, M., and Numa, S. (1987). Functional properties of nicotinic acetylcholine receptor subunits expressed in various combinations. *FEBS. Lett.* 214, 253-248.
23. Langosch, D., Thomas, L., and Betz, H. (1988). Conserved quaternary structure of ligand-gated ion channels: the postsynaptic glycine receptor is a pentamer. *Proc. Natl. Acad. Sci. USA* 85, 7394-7398.
24. Levitan, E. S., Schofield, P. R., Burt, D. R., Rhee, L. M., Wisden, W., Kohler, M., Fujita, N., Rodriquez, H. F., Stephenson, A., Darlison, M. G., Barnar, E. A., and Seeburg, P. H. (1988). Structural and functional basis for $GABA_A$ receptor heterogeneity. *Nature* 335, 76-79.
25. Lindstrom, J., Schoepfer, R., and Whiting, P. (1987). Molecular studies of the neuronal nicotinic acetylcholine receptor family. *Mol. Neurobiol.* 1, 281-337.
26. Loring, R. H., Chiappinelli V. A., Zigmond, R. E., and Cohen, J. B. (1984). Characterization of a snake venom neurotoxin which blocks nicotinic transmission in the avian ciliary ganglion. *Neuroscience* 11, 989-999.
27. Luetje, C., Wada, K., Rogers, S., Abramson, S., Tsuji, K., Heinemann, S. and Patrick, J., (1990). Neurotoxins distinguish between different neuronal nicotinic acetylcholine receptor subunits combinations. *J. Neurochem.*, In Press.
28. Maniatis, T., Fritsch, E. F., and Sambrook, J. (1982). *Molecular Cloning: A Laboratory Manual* (Cold Spring Harbor, N.Y.: Cold Spring Harbor Laboratory).
29. Mishina, M., Takai, T., Imoto, K., Noda, M., Takahashi, T., Numa, S., Methfessel, C., and Sakmann, B. (1986). Molecular distinction between fetal and adult forms of muscle acetylcholine receptor. *Nature* 321, 406-411.
30. Nagamine, Y., Sudol, M., and Reich, E. (1983). Hormonal regulation of plasminogen activator mRNA production in porcine kidney cells. *Cell* 32, 1181-1190.
31. Nef, P., Oneyser, C., Alliod, C., Courturier, S., and Ballivet, M. (1988). Genes expressed in the brain define three distinct neuronal nicotinic acetylcholine receptors. *EMBO J.* 7, 595-601.
32. Noda, M., Takahashi, H., Tanabe, T., Toyosato, M., Furutani, Y., Hirose, T., Asai, M., Inayama, S., Miyata, T., and Numa, S. (1982). Primary structure of $\alpha$-subunit precursor of *torpedo californica* acetyltylcholine receptor deduced from cDNA sequence. *Nature* 299, 793-797.

33. Obata, K. (1974). Transmitter sensitivities of some nerve and muscle cells in culture. *Brain Res.* 73, 71–88.
34. Patrick, J., and Stallcup, W. (1977). Immunological distinction between acetylcholine receptor and the alpha-bungarotoxin-binding component on sympathetic neurons. *Proc. Natl. Acad. Sci. USA* 74, 4689–4692.
35. Pritchett, D. B., Sontheimer, H., Gorman, C. M., Kettenmann, H., Seeburg, P. H., and Schofield, P. R. (1988). Transient expression shows ligand gating and allosteric potentiation of $GABA_A$ receptor subunits. *Science* 242, 1396–1308.
36. Pritchett, D. B., Sontheimer, H., Shrivers, B. D., Ymer, S., Kettenmann, H., Schofield, P. R., and Seeburg, P. H. (1989). Importance of a novel $GABA_A$ receptor subunit for benzodiazepine pharmacology. *Nature* 338, 582–585.
37. Ravdin, P., and Berg, D. K. (1979). Inhibition of neuronal acetylcholine sensitivity by α-toxins from *Bungarus multicinctus* venom. *Proc. Natl. Acad. Sci. USA* 76, 2072–2076.
38. Reynolds, J. A., and Karlin, A. (1978). Molecular weight in detergent solution of acetylcholine receptor from *Torpedo californica*. *Biochemistry* 17, 2035–2038.
39. Sakmann B., and Brenner, H. R. (1978). Change in synaptic channel gating during neuromuscular development. *Nature* 276, 401–402.
40. Schoepfer, R., Whiting, P., Esch, F., Blacher, R., Shimasaki, S., and Lindstrom, J. (1988). cDNA clones coding for the structural subunit of a chicken brain nicotinic acetylcholine receptor. *Neuron* 1, 241–248.
41. Schofield, P. R., Darlison, M. G., Fujita, N., Burt, D. R., Stephenson, F. A., Rodriquez, H., Rhee, L. M., Ramachandran, J., Reale, V., Glencorse, T. A., Seeburg, P. H. and Barnard, E. A. (1987). Sequence and functional express on the $GABA_A$ receptor shows a ligand-gated receptor super-family. *Nature* 328, 221–227.
42. Short, J. M., Fernandez, J. M., Sorge, J. A., and Huse, W. D. (1988). λZAP: a bacteriophage λ expression vector with in vivo excision properties. *Nucl. Acids Res.* 16, 7583–7600.
43. Sierra, F., Pittet, A., and Schibler, U. (1986). Different tissue-specific expression of the amylase gene Amy-1 in mice and rats. *Mol. Cell. Biol.* 6, 4067–4076.
44. Staden, R. (1984). Computer methods to locate signals in nucleic acid sequences. *Nucl. Acids Res.* 12, 505–519.
45. von Heijne, G. (1986). A new method for predicting signal sequence cleavage sites. *Nucl. Acids Res.* 14, 4683–4691.
46. Wada, K., Ballivet, M., Boulter, J., Connolly, J., Wada, E., Deneris, E., Swanson, L. W., Heinemann, S., and Patrick, J. (1988). Functional expression of a new pharmacological subtype of brain nicotinic acetylcholine receptor. *Science* 240, 330–334.
47. Wada, E., Wada, K., Boulter, J., Deneris, E., Heinemann, S., Patrick, J., and Swanson, L. W. (1989). Distribution of apha2, alpha3, alpha 4, and beta2 neuronal nicotinic receptor subunit mRNAs in the central nervous system: a hybridization histochemical study in the rat. *J. Comp. Neurol.* 284, 314–335.
48. Whiting, P. J., and Lindstrom, J. M. (1986). Purification and characterization of a nicotinic acetylcholine receptor from chick brain. *Biochemistry* 25, 2082–2093.
49. Whiting, P., and Lindstrom, J. (1987). Purification and characterization of a nicotinic acetylcholine receptor from rat brain. *Proc. Natl. Acad. Sci. USA* 84, 595–599.
50. Whiting, P., Esch, F., Shimasaki, S., and Lindstrom, J. (1987). Neuronal nicotinic acetylcholine receptor β-subunit is coded for by the cDNA clone α4. *FEBS Lett.* 2, 459–463.
51. Yanish-Perron, C., Vieira, J., and Messing, J. (1985). Improved M13 phage cloning vectors and host strains: nucleotide sequences of the M13mp18 and pUC19 vectors. *Gene* 33, 103–119.

SPECIFICATION SUMMARY

From the foregoing description, one of ordinary skill in the art can understand that the present invention is the discovery and isolation of DNA sequences that encode a new subunit member of the family of mammalian neuronal nicotinic acetylcholine receptors that are expressed in the central nervous system. The new mammalian neuronal nicotinic acetylcholine subunit is the beta4 subunit, which is useful alone or in functional combination with other subunits, including but not limited to, alpha2, alpha3, alpha4 and beta2.

Both the receptor subunit gene and proteins of the present invention can be used for drug design and screening. For example, the cDNA clone encoding the beta4 receptor subunit can be transcribed in vitro to produce mRNA. This mRNA, either from a single subunit clone or from a combination of clones, can then be injected into oocytes where it will direct the synthesis of the receptor molecule(s). Alternatively, the clones may be placed downstream appropriate gene regulatory elements and inserted into the genome of eukaryotic cells. This will result in transfected cell lines expressing one specific receptor subtype, or combinations of subtypes. The derived cell lines can then be produced in quantity for reproducible quantitative analysis of the effects of drugs on receptor function.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. Recombinant DNA encoding a beta4 neuronal nicotinic acetylcholine receptor subunit having the amino acid sequence as in FIG. 4.

2. DNA according to claim 1 wherein said DNA is capable of hybridizing to the nucleotide sequence set forth in FIG. 3 under high stringency conditions.

3. Recombinant DNA comprising a replicable vector containing DNA according to claim 2.

4. DNA according to claim 2 wherein said DNA has the same nucleotide sequence as nucleotides 1–1560 as shown in FIG. 3.

5. Recombinant DNA comprising a replicable vector containing DNA according to claim 4.

6. Cells containing the DNA of claim 1.

7. A method for producing beta4 neuronal nicotinic acetylcholine receptor subunit, said method comprising expressing DNA according to claim 1 in a suitable host.

8. Recombinant DNA comprising a replicable vector containing DNA according to claim 1.

9. Cells containing the vector of claims 8.

10. Recombinant messenger RNA complementary to the DNA of claim 1.

11. A method for detecting compounds that bind to nicotinic acetylcholine receptors, said method comprising contacting test cells with labeled compound, and thereafter determining the presence of labeled compound bound to test cells, wherein test cells express nicotinic acetylcholine cell surface receptors containing at least one beta4 subunit encoded by the mRNA of claim 10, wherein said mRNA is derived from a source other than said test cell.

12. A method of identifying compounds that are neuronal nicotinic acetylcholine receptor agonists, said method comprising comparing the response of test cells in the presence of said compound, relative to the response of said test cells in the absence of said compound, wherein test cells express nicotinic acetylcholine cell surface receptors containing at least one beta4 subunit encoded by the mRNA of claim 10, wherein said mRNA is derived from a source other than said test cell.

13. A method of identifying compounds that are neuronal nicotinic acetylcholine receptor antagonists, said method comprising:

contacting test cells with increasing concentrations of said compound in the presence of a fixed concentration of a neuronal nicotinic acetylcholine agonist, and detecting any difference in the response of test cells to agonist in the presence of said compound, relative to the response of said test cells in the absence of said compound, wherein test cells express nicotinic acetylcholine cell surface receptors containing at least one beta4 subunit encoded by the mRNA of claim 10, wherein said mRNA is derived from a source other than said test cell.

14. A method for detecting compounds that bind to nicotinic acetylcholine receptors, said method comprising contacting test cells with labeled compound, and thereafter determining the presence of labeled compound bound to test cells, wherein test cells express nicotinic acetylcholine cell surface receptors containing at least one beta4 subunit encoded by the DNA of claim 1, wherein said DNA is derived from a source other than said test cell.

15. A method of identifying compounds that are neuronal nicotinic acetylcholine receptor agonists, said method comprising comparing the response of test cells in the presence of said compound, relative to the response of said test cells in the absence of said compound, wherein test cells express nicotinic acetylcholine cell surface receptors containing at least one beta4 subunit encoded by the DNA of claim 1, wherein said DNA is derived from a source other than said test cell.

16. A method of identifying compounds that are neuronal nicotinic acetylcholine receptor antagonists, said method comprising:

contacting test cells with increasing concentrations of said compound in the presence of a fixed concentration of a neuronal nicotinic acetylcholine agonist, and detecting any difference in the response of test cells to agonist in the presence of said compound, relative to the response of said test cells in the absence of said compound, wherein test cells express nicotinic acetylcholine cell surface receptors containing at least one beta4 subunit encoded by the DNA of claim 1, wherein said DNA is derived from a source other than said test cell.

17. Plasmid pZPC13, ATCC No. 67893.

18. Recombinant DNA encoding the beta4 subunit protein encoded by the plasmid pZPC13, ATCC No. 67893.

19. Recombinant DNA comprising a replicable vector containing DNA according to claim 18.

20. DNA according to claim 18 wherein said DNA is capable of hybridizing to the beta4-subunit encoding portion of plasmid pZPC13 under high stringency conditions.

21. Recombinant DNA comprising a replicable vector containing DNA according to claim 20.

* * * * *